US008119103B2

(12) United States Patent
Moore

(10) Patent No.: US 8,119,103 B2
(45) Date of Patent: Feb. 21, 2012

(54) BIFUNCTIONAL RESORCINOL, THIORESORCINOL, AND DITHIORESORCINOL DERIVATIVE METAL CHELATING CONJUGATES

(75) Inventor: Dennis A. Moore, St. Louis, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 560 days.

(21) Appl. No.: 12/280,370

(22) PCT Filed: Feb. 20, 2007

(86) PCT No.: PCT/US2007/004427
§ 371 (c)(1),
(2), (4) Date: Aug. 22, 2008

(87) PCT Pub. No.: WO2007/100563
PCT Pub. Date: Sep. 7, 2007

(65) Prior Publication Data
US 2009/0082324 A1 Mar. 26, 2009

Related U.S. Application Data

(60) Provisional application No. 60/784,363, filed on Mar. 21, 2006, provisional application No. 60/776,785, filed on Feb. 24, 2006.

(51) Int. Cl.
*A61K 49/00* (2006.01)
(52) U.S. Cl. ...... 424/9.1; 424/1.11; 424/1.49; 424/1.65; 424/1.69; 424/1.73; 534/7; 534/14
(58) Field of Classification Search ............. 424/1.11, 424/1.49, 1.53, 1.65, 1.69, 1.73, 9.1, 9.2, 424/9.3, 9.4, 9.5, 9.6; 534/7, 10–16; 540/1, 540/450
See application file for complete search history.

(56) References Cited

U.S. PATENT DOCUMENTS

| 5,147,632 A | 9/1992 | Pan et al. |
| 5,186,923 A | 2/1993 | Piwnica-Worms et al. |
| 5,198,564 A | 3/1993 | Qianhuan |
| 5,310,539 A | 5/1994 | Williams |
| 5,435,990 A | 7/1995 | Cheng et al. |
| 5,559,149 A | 9/1996 | Clum et al. |
| 6,143,274 A | 11/2000 | Tweedle et al. |
| 6,602,989 B1 | 8/2003 | Sadik et al. |
| 6,916,460 B2 | 7/2005 | Murray et al. |
| 2003/0073856 A1 | 4/2003 | Hancu et al. |
| 2003/0161862 A1 | 8/2003 | Hizukuri et al. |
| 2005/0009760 A1 | 1/2005 | Wang et al. |
| 2005/0265940 A1 | 12/2005 | Liu |

FOREIGN PATENT DOCUMENTS

| EP | 976 392 | 2/2000 |
| GB | 1429373 | 3/1976 |
| JP | 60048916 | 3/1985 |
| JP | 10053515 | 2/1998 |
| JP | 10130155 | 5/1998 |
| WO | WO 01/60337 | 8/2001 |
| WO | WO 2007/064661 | 6/2007 |

OTHER PUBLICATIONS

Siemann et al (Biochimica et al Biophysica Acta 1571, 2002, pp. 190-200).*
Gu et al., "A Convenient Method of meta-Directing Nitration of 3-substituted Phenol by Lanthanide(III) Nitrates", Synth. Comm., 27(16), 1997, pp. 2793-2797.
Cacheris et al., "The Relationship Between Thermodynamics and the Toxicity of Gadnolinium Complexes", 1990, Magnetic Resonance Imaging, vol. 8 (4).
Spiegel et al., "And use of Nonaqueous Solvents in Parenteral Products", Journal of Pharmaceutical Sciences, 1963, vol. 52, No. 10, pp. 917-927.
Bergeron et al., "Desferrithiocin analogue based hexacoordinate iron(III) chelators", Journal of Medicinal Chemistry, American Chemical Society, 2003, vol. 46, No. 1, pp. 16-24, XP002265511.
Sugii et al., "Preparation and properties of a chelating resin containing the nitriosoresorcinol group", Talanta, 1979, vol. 26, No. 10, pp. 970-972, XP 002464399.
Mathias et al., "N N' Bis-2-Hydroxybenzyl-1-4-Bromoacetamidobenz YL-1 2-Ethylendiamine-N N'-Diacetic Acid a New Bifunctional Chelate for Radiolabeling Antibodies", Bioconjugate Chemistry, 1990, vol. 1, No. 3, pp. 204-211, XP 002464401.
Woods et al., "Synthesis and luminescence studies of aryl substituted tetraamide complexes of europium(III): a new approach to pH responsive luminescent europium probes", Inorganic Chemistry, Jul. 14, 2003, vol. 42, No. 14, pp. 4401-4408, XP 002464402.
Jones-Wilson et al., "New Hydroxybenzyl and Hydroxypyridylmethyl Substituted Triazacyclononane Ligands for Use with Gallium(III) and Indium(III)", Nuclear Medicine and Biology, 1995, vol. 22, No. 7, pp. 859-868, XP 001004873.
Sharma et al., "Inhibitory activity of polyhydroxycarboxylate chelators against recombinant NF-KB p50 protein-DNA binding", Bioorganic Chemistry, 2005, 33(2), pp. 67-81.
Xu et al., "Synthesis of new potential chelating agents: catecholbisphosphonate conjugates for metal intoxication therapy", Heteroatom Chemistry, 2004, 15(3), pp. 251-257.
Strivastava et al., "Metal chelators/antioxidants: Approaches to protect Erythrocytic Oxidative stress injury during Plasmodium Berghei infection in Mastomys choucha", Pharmacological Research, 1999, 40(3), pp. 239-241.
Anson et al., Organometallic flavonoid derivatives as spectroscopic probes, Bioorganic & Medicinal Chemistry Letters, 1998, 8(24), pp. 3549-3554.
Van Acker et al., "Influence of iron chelation on the antioxidant activity of flavonoids", Biochemical Pharmacology, 1998, 56(8), pp. 935-943.

(Continued)

Primary Examiner — D L Jones

(57) ABSTRACT

The present invention is directed to metal chelating conjugates for use as metallopharmaceutical diagnostic or therapeutic agents. Specifically, conjugates of the present invention include one or more carriers, a linker, and metal coordinating moiety comprising a resorcinol, thioresorcinol, or dithioresorcinol derivative through which the metal coordinating moiety is bonded to the linker.

20 Claims, No Drawings

OTHER PUBLICATIONS

Martin et al., "Bio-assays of humic-like model compounds: chelation versus acid-base effects", Journal of Enviromental Science and Health, Part A: Environmental Science and Engineering, 1989, A24(2), pp. 167-174.

Mgaloblishvili et al., "Effect of Chelates and clinoptilolite-rich tuffs on biochemical indexes of tea leaf quality", Soobshcheniya Akademii Nauk Gruzinskoi SSR, 1987, 128(2), pp. 401-404.

White et al., "The use of Chang cells cultured in vitro to evaluate potential iron chelating drugs", British Journal of Haematology, 1976, 33(4), pp. 487-494.

McGinity et al., "Influence of peroxide impurities in polyethylene glycols on drug stability", Journal of Pharmaceutical Sciences, 1975, 64(2), pp. 356.

Desai et al., "2, 4, 6-Trihydroxy-substituted compounds as indicators for the EDTA titration of iron", Journal of the Institution of Chemists (India), 1971, 43(pt. 5), pp. 179-182.

Clemetson et al., "Plant polyphenols as antioxidants for ascorbic acid", Annals of the New York Academy of Sciences, 1966, 136(14), pp. 339-376.

* cited by examiner

BIFUNCTIONAL RESORCINOL, THIORESORCINOL, AND DITHIORESORCINOL DERIVATIVE METAL CHELATING CONJUGATES

CROSS REFERENCE TO RELATED APPLICATIONS

This application is a national stage application of PCT/US2007/004427, filed Feb. 20, 2007, which claims the benefit of U.S. Provisional Application No. 60/784,363 filed Mar. 21, 2006 and U.S. Provisional Application No. 60/776,785 filed Feb. 24, 2006.

BACKGROUND

The present invention is generally directed to metal chelating conjugates for use as a metallopharmaceutical diagnostic or therapeutic agent.

Metallopharmaceutical diagnostic and therapeutic agents are finding ever-increasing application in biological and medical research, and in diagnostic and therapeutic procedures. Generally, these agents contain a radioisotope or paramagnetic metal which upon introduction to a subject, become localized in a specific organ, tissue or skeletal structure of choice. When the purpose of the procedure is diagnostic, images depicting the in vivo distribution of the radioisotope, paramagnetic or radioopaque metal can be made by various means, including single photon emission, magnetic resonance and x-ray, depending on the metal selected and substitution pattern on the metal complex. The distribution and corresponding relative intensity of the detected radioisotope, paramagnetic or radioopaque metal not only indicates the space occupied by the targeted tissue, but may also indicate a presence of receptors, antigens, aberrations, pathological conditions, and the like. When the purpose of the procedure is therapeutic, the agent typically contains a radioisotope and the radioactive agent delivers a dose of radiation to the local site.

Depending upon the target organ or tissue of interest and the desired diagnostic or therapeutic procedure, a range of metallopharmaceutical agents may be used. One common form is a conjugate comprising a radioactive or paramagnetic metal, a carrier agent for targeting the conjugate to a specific organ or tissue site, and a linkage for chemically linking the metal to the carrier. In such conjugates, the metal is typically associated with the conjugate in the form of a coordination complex, more typically as a chelate of a macrocycle. See, e.g., Liu, U.S. Pat. No. 6,916,460.

In U.S. Pat. No. 6,143,274, Tweedle et al. disclose a method for imaging mammalian tissue utilizing a non-ionic complex of a paramagnetic ion of a lanthanide element and a macrocyclic chelating agent. A non-ionic complex, however, is less stable than an anionic complex (i.e., the anionic complex tends to exhibit stronger electrostatic interaction between the cationic metal and anionic ligand).

Metallopharmaceuticals utilizing metal coordinating moieties having a hydroxybenzyl group to assist in the coordination are well known, e.g., HBED. It has been well-demonstrated that the phenolic oxygen, in concert with an aminomethyl moiety situated in an ortho relationship thereto, presents a good chelate forming group for many metals. The need for creating metal coordinating groups that demonstrate higher affinity for metals remains important, however, to reduce the overall toxicity of these compounds. Martell et al. disclose a general description of relevant chelates and metal-binding moieities, while Cacheris et al. recite the importance of the selectivity of chelates for exogenous versus endogenous metals for controlling toxicity (see, A. Martell and R. Smith, *Critical Stability Constants, Volume 1: Amino Acides,* Plenum Press (1974) and W. Cacheris et al., *The Relationship Between Thermodynamics and the Toxicity of Gadnolinium Complexes,* Magnetic Resonance Imaging, 8(4), (1990)).

SUMMARY

Among the several aspects of the present invention is the provision of a conjugate for use in diagnostic and therapeutic procedures. Advantageously, such conjugates tend to accumulate in the specific organ, tissue or skeletal structure with a reduced risk of non-specific binding to non-target tissues, thereby allowing for the conjugates to be targeted to specific disease states, if desired. Further, these conjugates may be formed at relatively low temperatures, thereby decreasing the chance that a carrier for targeting the conjugate to a biological tissue or organ will be destroyed during the complexation reaction.

Briefly, therefore, the present invention is directed to a conjugate, the conjugate comprising one or more carriers for targeting the conjugate to a biological tissue or organ, a metal coordinating moiety, and a linker chemically linking the metal coordinating moiety to the carrier, the metal coordinating moiety comprising a resorcinol, thioresorcinol, or dithioresorcinol derivative through which the metal coordinating moiety is bonded to the linker.

The present invention is further directed to a conjugate, the conjugate comprising one or more carriers for targeting the conjugate to a biological tissue or organ, a metal coordinating moiety, a metal complexed by the metal coordinating moiety, and a linker chemically linking the metal coordinating moiety to the carrier, the metal coordinating moiety comprising a resorcinol, thioresorcinol, or dithioresorcinol derivative through which the metal coordinating moiety is bonded to the linker.

The present invention is further directed to a diagnostic or therapeutic method. The method comprises administering a conjugate to a subject, the conjugate comprising one or more carriers for targeting the conjugate to a biological tissue or organ, a metal coordinating moiety, a radioactive, paramagnetic or radioopaque metal complexed by the metal coordinating moiety, and a linker chemically linking the metal coordinating moiety to the carrier, the metal coordinating moiety comprising a resorcinol, thioresorcinol, or dithioresorcinol derivative through which the metal coordinating moiety is bonded to the linker.

The present invention is further directed to a kit for the preparation of a metallopharmaceutical. The kit comprises a conjugate for use in a diagnostic or therapeutic method, the conjugate comprising one or more carriers for targeting the conjugate to a biological tissue or organ, a metal coordinating moiety, a metal complexed by the metal coordinating moiety, and a linker chemically linking the metal coordinating moiety to the carrier, the metal coordinating moiety comprising a resorcinol, thioresorcinol, or dithioresorcinol derivative through which the metal coordinating moiety is bonded to the linker.

Other aspects of the invention will be in part apparent and in part pointed out hereinafter.

DETAILED DESCRIPTION OF VARIOUS EMBODIMENTS

The present invention provides conjugates that can rapidly form coordination complexes with metals for use in diagnostic or therapeutic metalloradiopharmaceuticals, or magnetic resonance imaging contrast agents. The conjugates can also serve as bifunctional chelators (BFC's) for attaching metal ions to bio-directing carriers, sometimes referred to as biomolecules, that bind in vivo to a tissue type, organ or other biologically expressed composition or receptor. The target-specific metallopharmaceuticals of the present invention are useful in the diagnosis of disease by magnetic resonance imaging or scintigraphy or in the treatment of disease by systemic radiotherapy.

Generally, the conjugates of the present invention comprise a bio-directing carrier and a metal coordinating moiety covalently joined indirectly through a linker, the linker being chemically bonded to the metal coordinating moiety via a resorcinol, thioresorcinol, or dithioresorcinol derivative (sometimes collectively referred to as ((di)thio)resorcinol). Thus, the ((di)thio)resorcinol derivatives of the present invention have the general formula

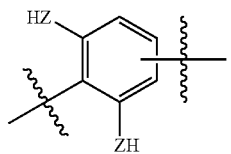

wherein each Z is independently an oxygen or a sulfur atom.

Without being held to any particular theory, it is believed that the orientation of the hydroxyl and/or thiol groups of the ((di)thio)resorcinol derivative at the two positions ortho to the carbon at the point of attachment of the metal chelator (see Formula (A) below) offers a more robust coordination environment for the metal. For example, it is known that yttrium-oxygen coordination bonds are quite labile. Thus, in solution this bond is breaking and reforming very rapidly. The availability of the second positionally equivalent, phenolic oxygen (in the case of the resorcinol derivative) allows for quick reformation of the oxygen-metal bond. Consequently, the second oxygen provides an intramolecular competitive binding event versus any external competition, which could lead to decomplexation and decomposition of the radioisotope-complex. Similarly, because many metals form stable coordination bonds with thiol groups, one or both of the hydroxyl groups may be replaced with a thiol group.

The linker may be attached to the ((di)thio)resorcinol derivative at any available position. The remainder of the metal coordinating moiety, designated herein as the "metal chelator", is attached to the ((di)thio)resorcinol ring at the carbon atom ortho to both carbon atoms substituted by the ZH groups. Thus, schematically, a conjugate comprising the bio-directing carrier, the linker, and the metal coordinating moiety comprising the ((di)thio)resorcinol derivative of the present invention corresponds to Formula (A)

Formula (A)

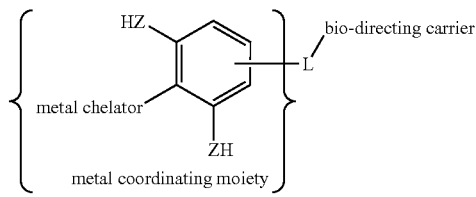

wherein

L covalently bonds, either directly or indirectly, the metal coordinating moiety to the bio-directing carrier; and each Z is independently oxygen or sulfur.

Although Formula (A) depicts only a single bio-directing carrier, it is contemplated that a conjugate may comprise multiple bio-directing carriers, each of which is connected to the metal coordinating moiety via the linker, L. This linker may range from a single covalent bond to a carbohydrate group having bonds with several bio-directing carriers as more fully described below. The linking moieties are used to directly impact characteristics of the metallophramaceutical such as potency for the bio-directing carriers target, biodistribution, elimination route from the body and stability of the drug substance or product.

Prior to use in a diagnostic or therapeutic procedure, a conjugate corresponding to Formula A is complexed with a metal to form a metallopharmaceutical diagnostic or therapeutic agent of the present invention.

Bio-Directing Carriers

As previously noted, conjugates of the present invention include one or more bio-directing carriers, also known as biomolecules, that direct the conjugate to the desired tissue, organ, receptor or other biologically expressed composition target. Ideally, the carrier is selective or specific for the targeted organ or tissue site.

Typical bio-directing carriers include hormones, amino acids, peptides, peptidomimetics, proteins, nucleosides, nucleotides, nucleic acids, enzymes, carbohydrates, glycomimetics, lipids, albumins, mono- and polyclonal antibodies, receptors, inclusion compounds such as cyclodextrins, and receptor binding molecules, e.g., $\alpha_v\beta_3$. Specific examples of carriers include steroid hormones for the treatment of breast and prostate lesions; somatostatin, bombesin, CCK, and neurotensin receptor binding molecules for the treatment of neuroendocrine tumors; CCK receptor binding molecules for the treatment of lung cancer; ST receptor and carcinoembryonic antigen (CEA) binding molecules for the treatment of colorectal cancer; dihyroxyindolecarboxylic acid and other melanin producing biosynthetic intermediates for the treatment of melanoma; integrin receptor and atherosclerotic plaque binding molecules for the treatment of vascular diseases; and amyloid plaque binding molecules for the treatment of brain lesions. Exemplary bio-directing carriers also include synthetic polymers such as polyaminoacids, polyols, polyamines, polyacids, oligonucleotides, aborols, dendrimers, and aptamers.

In one embodiment, the bio-directing carrier is selected from among amides, ethers, antibodies (e.g., NeutroSpect®, Zevalin®, and Herceptin®), proteins (e.g., TCII, HSA, annexin, and Hb), peptides (e.g., octreotide, bombesin, neurotensin, and angiotensin), nitrogen-containing simple or complex carbohydrates (e.g., glucosamine and glucose), nitrogen-containing vitamins (e.g., vitamin A, B1, B2, B12, C, D2, D3, E, H, and K), nitrogen-containing hormones (e.g., estradiol, progesterone, and testosterone), nitrogen-containing active pharmaceuticals (e.g., celecoxib or other nitrogen-containing NSAIDS, AMD3100, CXCR4 and CCR5 antagonists) or nitrogen-containing steroids. In one example of this embodiment, the biomolecules are selected from among imidazole, triazole, a peptide, a nitrogen-substituted simple or complex carbohydrate, a nitrogen-substituted vitamin, and a nitrogen-substituted small molecule. In another example, the biomolecules are imidazole, triazole, the N-terminus of a peptide, a nitrogen-substituted simple or complex carbohydrate or a nitrogen-substituted vitamin.

In another embodiment, the bio-directing carrier is added to a reactive ((di)thio)resorcinol derivative. For instance, the linker may be selected from imidazole-carbonyl or triazole-carbonyl, N-hydroxysuccinimide ester, p-nitrophenyl ester or other commonly used leaving groups (see, e.g., Pearson and Roush, *Handbook of Reagents for Organic Synthesis: Activating Agents and Protecting Groups* or Bodansky, *Peptide Chemistry: A Practical Textbook*) presenting a complex with a substitutionally-reactive moiety. The triazole, imidazole or reactive ester may be displaced by the addition of a bio-directing carrier possessing a nucleophilic moiety forming a new urea or amide bond.

To increase specificity for a particular target tissue, organ receptor or other biologically expressed composition, multiple bio-directing carriers may be utilized. In such instances, the biodirecting carriers may be the same or different. For example, a single conjugate may possess multiple antibodies or antibody fragments, which are directed against a desired antigen or hapten. Typically, the antibodies used in the conjugate are monoclonal antibodies or antibody fragments that are directed against a desired antigen or hapten. Thus, for example, the conjugate may comprise two or more monoclonal antibodies having specificity for a desired epitope thereby increasing concentration of the conjugate at the desired site. Similarly and independently, a conjugate may comprise two or more different bio-directing carriers each of which is targeted to a different site on the same target tissue or organ. By utilizing multiple bio-directing carriers in this manner, the conjugate advantageously concentrates at several areas of the target tissue or organ, potentially increasing the effectiveness of therapeutic treatment. Further, the conjugate may have a ratio of bio-directing carriers designed to concentrate the conjugate at a target tissue or organ that optimally achieves the desired therapeutic and/or diagnostic results.

Linker

As previously noted, the bio-directing carrier(s) are covalently bonded to the ((di)thio)resorcinol derivative of the metal coordinating moiety via a linker, L. While the linker is preferably attached at a position meta to the hydroxyl and/or thiol groups of the ((di)thio)resorcinol derivative, attachment at either of the positions ortho to a hydroxyl and/or thiol group of the ((di)thio)resorcinol derivative are contemplated by this invention.

Further, the linker selected should not interfere with the accumulation of the conjugate in the specific organ, tissue or skeletal structure. In some instances, the linker may aid the accumulation of the conjugates of the present invention in the specific organ, tissue or skeletal structure with a reduced risk of non-specific binding to non-target tissues.

The linker may be modified or synthesized such that it bonds to multiple bio-directing carriers and/or affects the biodistribution of the conjugate. For example, the linker may comprise a $C_4$-$C_{20}$ carbohydrate moiety, the carbohydrate moiety having the capacity to bind one or more bio-directing carriers through ether linkages. In addition, the carbohydrate moiety increases the water solubility of the conjugate thereby affecting biodistribution In one embodiment, L is selected from the group consisting of $C_{1-10}$ alkylene, oxygen, sulfur, keto (—C(O)—), amino (—NH—), amido (—C(O)NH—), urea (—NHC(O)NH—), thiourea (—NHC(S)NH—), ester (—C(O)O—), polyoxo (e.g., —O—$CH_2CH_2$—O—$CH_2CH_2$—O—), polyhydroxy (e.g., carbohydrates), and peptides, the alkylene, amino, amido, urea, and thiourea groups being optionally substituted with aryl, $C_{1-7}$ alkyl, $C_{1-7}$ hydroxyalkyl or $C_{1-7}$ alkoxyalkyl. In one example of this embodiment, L is selected from the group consisting of $C_{1-10}$ alkylene, oxygen, sulfur, keto, amino, amido, thiourea, ester, $C_4$-$C_{20}$ carbohydrate, the alkylene, amino, amido, and thiourea groups being optionally substituted with aryl, $C_{1-7}$ alkyl, $C_{1-7}$ hydroxyalkyl or $C_{1-7}$ alkoxyalkyl. By way of further example, L may be selected from a more restrictive group, e.g., amino, thiourea, monosaccharides (e.g., hexoses and pentoses) and disaccharides (e.g., sucrose). In one alternative of this embodiment, L comprises other than a urea linkage.

Metals

Any metal capable of being detected in a diagnostic procedure in vivo or in vitro or useful in the therapeutic treatment of disease can be employed as a metal in the present conjugates. Particularly, any radioactive metal ion or paramagnetic metal ion capable of producing a diagnostic result or therapeutic response in a human or animal body or in an in vitro diagnostic assay may be used. The selection of an appropriate metal based on the intended purpose is known by those skilled in the art. In one embodiment, the metal is selected from the group consisting of Lu, Lu-177, Y, Y-90, In, In-111, Tc, Tc=O, Tc-99m, Tc-99 m=O, Re, Re-186, Re-188, Re=O, Re-186=O, Re-188=O, Ga, Ga-67, Ga-68, Cu, Cu-62, Cu-64, Cu-67, Gd, Gd-153, Dy, Dy-165, Dy-166, Ho, Ho-166, Eu, Eu-169, Sm, Sm-153, Pd, Pd-103, Pm, Pm-149, Tm, Tm-170, Bi, Bi-212, As and As-211. For example, the metal may be selected from the group consisting of Y-90, In-111, Tc-99m, Re-186, Re-188, Cu-64, Ga-67, Ga-68 and Lu-177. By way of further example, the metal may be selected from a more restrictive group, e.g., Y-90, In-111, Tc-99m, Re-186, Cu-64, Ga-67, and Lu-177 or Y-90, In-111, and Tc-99m. In another embodiment, metals that form labile bonds with oxygen, such as yttrium and indium, are appropriate metals for metal coordinating moieties having a ((di)thio)resorcinol derivative.

Metal Coordinating Moiety

The metal coordinating moiety may be any moiety having a ((di)thio)resorcinol derivative used to complex (also referred to as "coordinate") one or more metals under physiological conditions. Preferably, the metal coordinating moiety forms a thermodynamically and kinetically stable complex with the metal to keep the complex intact under physiological conditions; otherwise, systemic release of the coordinated metal may result.

For ease of discussion, the metal coordinating moiety may be considered to consist of two components, (a) the metal chelator and (b) the ((di)thio)resorcinol derivative. Although not required, the oxygen or sulfur atoms comprising the hydroxyl or thiol groups, respectively, of the ((di)thio)resorcinol derivative may participate in the complexation of the metal. In other words, the metal coordinating moiety may complex the metal with or without the participation of the hydroxyl or thiol groups of the ((di)thio)resorcinol derivative. The participation of the hydroxyl or thiol groups of the ((di)thio)resorcinol derivative will depend upon the nature of the metal chelator and the particular metal selected. In one embodiment, the metal coordinating moiety corresponds to Formula (B):

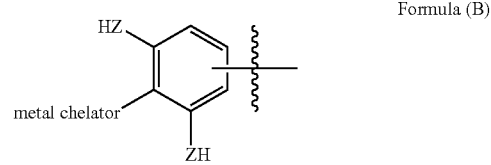

Formula (B)

wherein each Z is independently oxygen or sulfur.

In general, the metal coordinating moiety may be acyclic or cyclic. For example, metal coordinating moieties include polycarboxylic acids such as EDTA, DTPA, DCTA, DOTA, TETA, or analogs or homologs thereof. To provide greater stability under physiological conditions, however, macrocyclics, e.g., triaza and tetraza macrocycles, are generally preferred. In some embodiments, the macrocyclic metal coordinating moiety is cyclen or tacn.

In one embodiment, the metal coordinating moiety comprises a substituted heterocyclic ring where the heteroatom is nitrogen. Typically, the heterocyclic ring comprises from about 9 to about 15 atoms, at least 3 of these ring atoms being nitrogen. In one example of this embodiment, the heterocyclic ring comprises 3-5 ring nitrogen atoms where at least one of the ring nitrogen atoms is substituted. For these embodiments, the ring carbon atoms are optionally substituted. One such macrocycle corresponds to Formula (1):

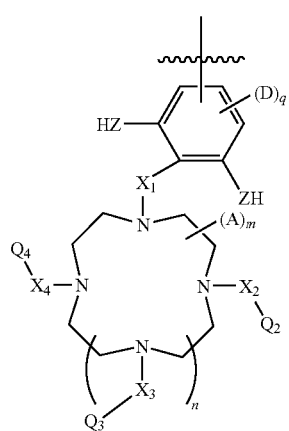
(1)

wherein
each Z is independently oxygen or sulfur;
n is 0, 1 or 2;
m is 0-20 wherein when m is greater than 0, each A is $C_{1-20}$alkyl or aryl optionally substituted by one or more aryl, $C_{1-20}$ alkyl, carbaldehyde, keto, carboxyl, cyano, halo, nitro, amido, sulfato, sulfito, phosphato phosphito, hydroxyl, oxy, ether, $C_{4-20}$ carbohydrate, mercapto or thio;
q is 0-3 wherein when q is greater than 0, each D is independently selected from the group consisting of fluoro, chloro, bromo, iodo, carboxyl, cyano, nitro, amido, hydroxyl, amino, sulfato, sulfito, phosphato, phosphito, ether, $C_{4-20}$ carbohydrate, aryl, and $C_{1-20}$ alkyl optionally substituted with one or more of $C_{1-20}$ alkyl, carboxyl, cyano, nitro, amido, hydroxyl, amino, sulfato, sulfito, phosphato, and phosphito;
$X_1, X_2, X_3$ and $X_4$ are independently optionally substituted methylene where the substituents are selected from the group consisting of aryl, $C_{1-20}$ alkyl, carbaldehyde, keto, carboxyl, cyano, halo, nitro, amido, sulfato, sulfito, phosphato phosphito, hydroxyl, oxy, ether, $C_{4-20}$ carbohydrate, mercapto and thio; and
$Q_2$-$Q_4$ are independently selected from the group consisting of:

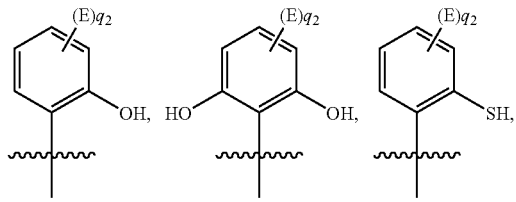

-continued

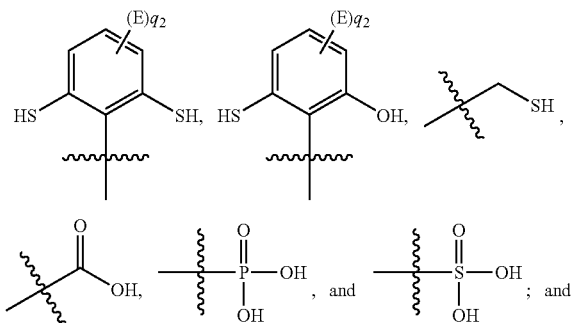

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, phosphito, phosphato ether, $C_{4-20}$ carbohydrate, and $C_{1-20}$ alkyl optionally substituted with one or more of $C_{1-20}$alkyl, carboxy, cyano, nitro, amido, hydroxyl, sulfito, phosphito, sulfato, and phosphato.

For metal coordinating moieties of Formula (1), the D substituent, if present, is independently bonded to any of the substitutable phenyl ring carbon atoms. In one embodiment, each D is fluoro, chloro, bromo, iodo, carboxyl, cyano, nitro, amido, hydroxyl, amino, sulfito, phosphito, sulfato, phosphato, ether, $C_{4-20}$ carbohydrate, aryl, or $C_{1-8}$ alkyl optionally substituted with one or more of $C_{1-20}$ alkyl, carboxyl, cyano, nitro, amido, hydroxyl, amino, sulfito, phosphito, sulfato, and phosphato. More typically, each D is bromo, iodo, carboxyl, or hydroxyl.

Further, for metal coordinating moieties of Formula (1), the E substituent, if present, is independently bonded to any of the substitutable phenyl ring carbon atoms. In one embodiment, each E is fluoro, chloro, bromo, iodo, carboxyl, cyano, nitro, amido, hydroxyl, amino, sulfito, phosphito, sulfato, phosphato, ether, $C_{4-20}$ carbohydrate, aryl, or $C_{1-8}$alkyl optionally substituted with one or more of $C_{1-20}$ alkyl, carboxyl, cyano, nitro, amido, hydroxyl, amino, sulfito, phosphito, sulfato, and phosphate. More typically, each E is bromo, Iodo, carboxyl, or hydroxyl.

Typically, for metal coordinating moieties of Formula (1), $X_1$-$X_4$ are independently methylene optionally substituted by $C_{1-6}$ alkyl, halo, or hydroxyl.

In another embodiment of metal coordinating moieties of Formula (1), $q_2$ is 0. Accordingly, $Q_2$, $Q_3$, and $Q_4$ are independently selected from the group consisting of:

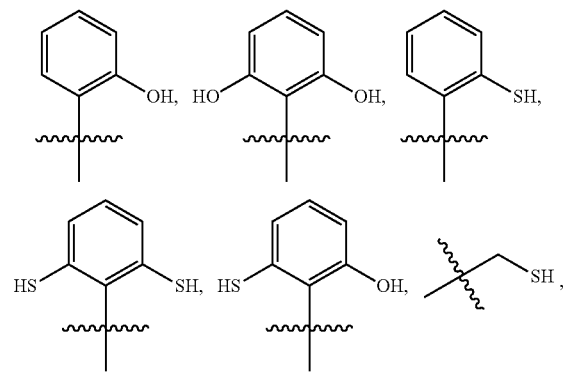

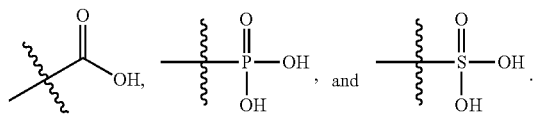

When the metal coordinating moiety corresponds to Formula (1) and m is greater than zero, it is generally preferred that each A be a substituent that positively impacts stability and biodistribution. When present, each A may independently be substituted with one or more aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto or thio substituents. In addition, when A is aryl or alkyl, each of these, in turn, may be optionally substituted with an aryl or $C_{1-20}$ alkyl moiety optionally substituted with one or more aryl, carbaldehyde, keto, carboxyl, cyano, halo, nitro, amido, sulfato, sulfito, phosphato, phosphito, hydroxyl, oxy, mercapto and thio.

Further, for the metal coordinating moieties of Formula (1), the A substituent, if present, is bonded to any of the ring carbon atoms. Further, each ring carbon atom may be substituted by one or two A substituents so that the number of possible A substituents varies with the number of ring carbon atoms. In one embodiment of metal coordinating moieties of Formula (1) having at least one A substituent, each A is independently aryl or $C_{1-8}$ alkyl optionally substituted with one or more aryl, keto, carboxyl, cyano, nitro, $C_{1-20}$ alkyl, amido, sulfato, sulfito, phosphato, phosphito, oxy and thio. For example, each A may be aryl or $C_{1-6}$ alkyl optionally substituted with one or more aryl, keto, amido and oxy. By way of further example, each A may be methyl.

In general, as the value of n increases, the size of the macrocycle increases. In this manner, the size of the macrocycle may be controlled to match the size and coordination capacity of the metal to be coordinated.

Exemplary metal coordinating moieties of Formula (1) include:

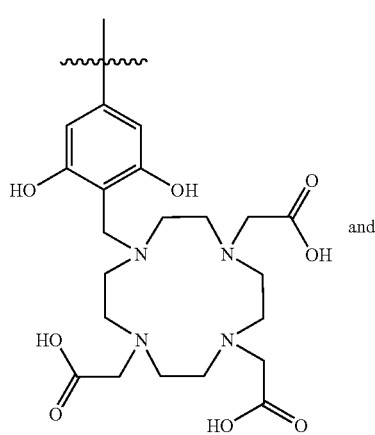

and

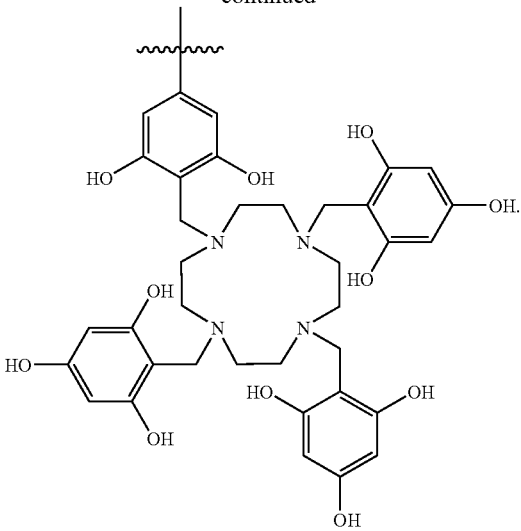

In addition to the metal coordinating moieties comprising a heterocyclic ring, the metal coordinating moieties may alternatively comprise a substituted chain of carbon and nitrogen atoms. As used herein the chain of nitrogen and carbon may be referred to as the "backbone" or the "chain of atoms". Typically, the chain of atoms comprises from about 4 to about 10 atoms, at least 2 of said atoms being nitrogen. Preferably, the chain of atoms comprises 2-4 nitrogen atoms wherein at least one of the chain nitrogen atoms is substituted. The backbone carbon atoms are optionally substituted. Typically, the backbone nitrogen atoms are separated from each other by two carbon atoms. In this embodiment, the metal coordinating moiety typically has the following Formula (2):

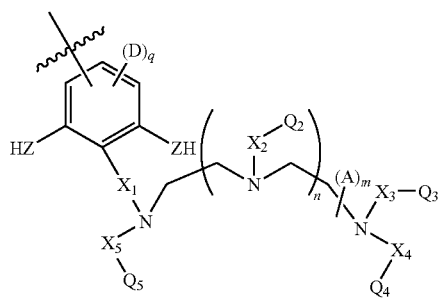

(2)

wherein
each Z is independently oxygen or sulfur;
n is 0, 1 or 2;
m is 0-12 wherein when m is greater than 0, each A is $C_{1-20}$alkyl or aryl optionally substituted by one or more aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto or thio;
q is 0-3 wherein when q is greater than 0, each D is independently selected from the group consisting of fluoro, chloro, bromo, iodo, carboxyl, cyano, nitro, amido, hydroxyl, amino, sulfato, sulfito, phosphato, phosphito, ether, $C_{4-20}$ carbohydrate, aryl, and $C_{1-20}$ alkyl optionally substituted with one or more of $C_{1-20}$alkyl, carboxyl, cyano, nitro, amido, hydroxyl, amino, sulfato, sulfito, phosphato, and phosphito;
$X_1$, $X_2$, $X_3$, $X_4$, and $X_5$ are independently optionally substituted methylene where the substituents are selected from the group consisting of aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto and thio;

$Q_2$-$Q_5$ are independently selected from the group consisting of:

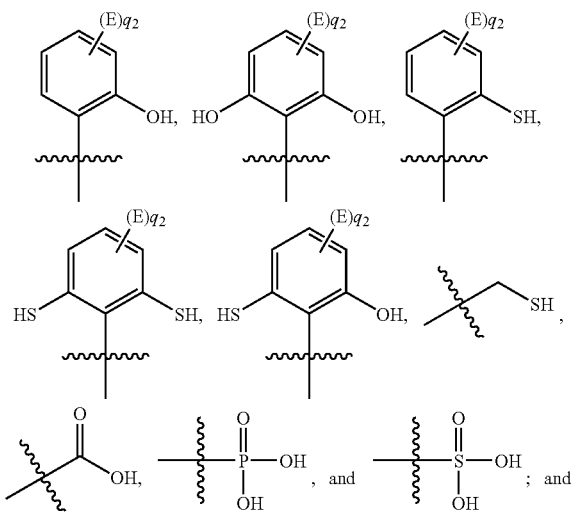

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, ether, $C_{4-20}$ carbohydrate, phosphito, and $C_{1-20}$ alkyl optionally substituted with one or more or $C_{1-20}$ alkyl, carboxy, cyano, nitro, amido, hydroxyl, sulfito, phospito, sulfato, and phosphato.

For metal coordinating moieties of Formula (2), the D substituent, if present, is independently bonded to any of the substitutable phenyl ring carbon atoms. In one embodiment, each D is fluoro, chloro, bromo, iodo, carboxyl, cyano, nitro, amido, hydroxyl, amino, sulfito, phosphito, sulfato, phosphato, ether, $C_{4-20}$ carbohydrate, aryl, or $C_{1-8}$ alkyl optionally substituted with one or more of $C_{1-20}$ alkyl, carboxyl, cyano, nitro, amido, hydroxyl, amino, sulfito, phosphito, sulfato, and phosphate. More typically, each D is bromo, iodo, carboxyl, or hydroxyl.

Further, for metal coordinating moieties of Formula (2), the E substituent, if present, is independently bonded to any of the substitutable phenyl ring carbon atoms. In one embodiment, each E is fluoro, chloro, bromo, iodo, carboxyl, cyano, nitro, amido, hydroxyl, amino, sulfito, phosphito, sulfato, phosphato, ether, $C_{4-20}$ carbohydrate, aryl, or $C_{1-8}$ alkyl optionally substituted with one or more of $C_{1-20}$ alkyl, carboxyl, cyano, nitro, amido, hydroxyl, amino, sulfito, phosphito, sulfato, and phosphate. More typically, each E is bromo, iodo, carboxyl, or hydroxyl.

Typically, for metal coordinating moieties of Formula (2), $X_1$-$X_4$ are independently methylene optionally substituted by $C_{1-6}$ alkyl, halo, or hydroxyl.

In another embodiment of metal coordinating moieties of Formula (2), $q_2$ is 0. Accordingly, $Q_2$, $Q_3$, $Q_4$ and $Q_5$ are independently selected from the group consisting of:

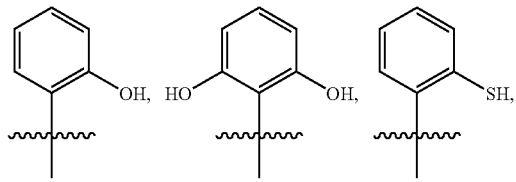

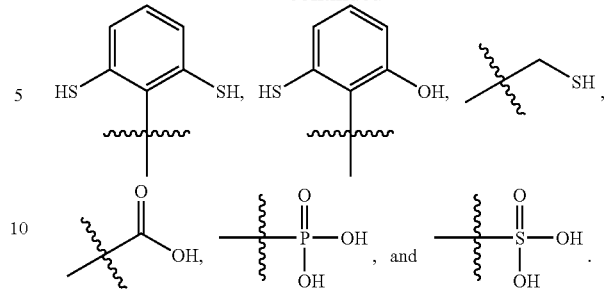

When the metal coordinating moiety corresponds to Formula (2) and m is greater than 0, it is generally preferred that each A be a substituent that positively impacts stability and biodistribution. When present, each A may independently be substituted with one or more aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto, or thio substituents. In addition, when A is aryl or alkyl, each of these, in turn, may be optionally substituted with an aryl or $C_{1-20}$ alkyl moiety optionally substituted with one or more aryl, carbaldehyde, keto, carboxyl, cyano, halo, nitro, amido, sulfato, sulfito, phosphato, phosphito, hydroxyl, oxy, mercapto and thio.

Further, for the metal coordinating moieties of Formula (2), the A substituent, if present, is bonded to any of the backbone carbon atoms. Further, each backbone carbon atom may be substituted by one or two A substituents so that the number of possible A substituents varies with the number of carbon atoms. In one embodiment of metal coordinating moieties of Formula (2) having at least one A substituent, each A is independently aryl or $C_{1-8}$ alkyl optionally substituted with one or more aryl, keto, carboxyl, cyano, nitro, $C_{1-20}$ alkyl, amido, sulfato, sulfito, phosphato, phosphito, oxy and thio. For example, each A may be aryl or $C_{1-6}$ alkyl optionally substituted with one or more aryl, keto, amido and oxy. By way of further example, each A may be methyl.

In general, as the value of n increases, the length of the chain of atoms increases. In this manner, the length of the backbone may be controlled to match the size and coordination capacity of the metal to be coordinated.

For any of the above embodiments, the metal coordinating moiety may be complexed with a metal, M, thereby forming a metal complex.

In one embodiment where the metal coordinating moiety is a heterocyclic ring and complexed with a metal, M, the complex has the following Formula (3):

(3)

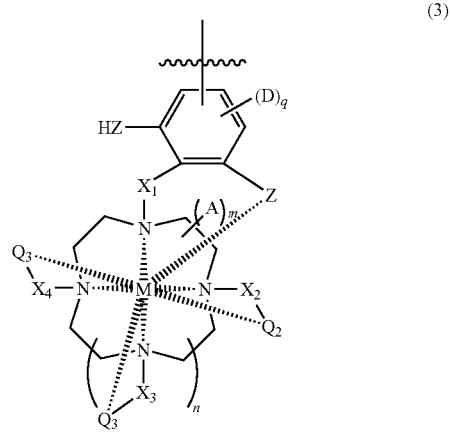

wherein
each Z is independently oxygen or sulfur;
n is 0, 1 or 2;
m is 0-20 wherein when m is greater than 0, each A is $C_{1-20}$ alkyl or aryl optionally substituted by one or more aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto or thio;
q is 0-3 wherein when q is greater than 0, each D is independently selected from the group consisting of fluoro, chloro, bromo, iodo, carboxyl, cyano, nitro, amido, hydroxyl, amino, sulfato, sulfito, phosphato, phosphito, ether, $C_{4-20}$ carbohydrate, aryl, and $C_{1-20}$ alkyl optionally substituted with one or more of $C_{1-20}$ alkyl, carboxyl, cyano, nitro, amido, hydroxyl, amino, sulfato, sulfito, phosphato, and phosphito;
$X_1$, $X_2$, $X_3$ and $X_4$ are independently optionally substituted methylene where the substituents are selected from the group consisting of aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto and thio:
$Q_2$-$Q_4$ are independently selected from the group consisting of:

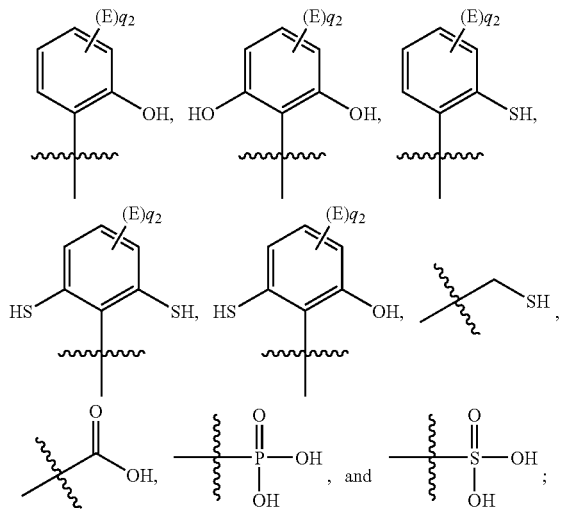

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, ether, $C_{4-20}$ carbohydrate, phosphito, and $C_{1-20}$ alkyl optionally substituted with one or more or $C_{1-20}$ alkyl, carboxy, cyano, nitro, amido, hydroxyl, sulfito, phospito, sulfato, and phosphate; and
M is selected from the group consisting of Lu, Lu-177, Y, Y-90, In, In-111, Tc, Tc=O, Tc-99m, Tc-99 m=O, Re, Re-186, Re-188, Re=O, Re-186=O, Re-188=O, Ga, Ga-67, Ga-68, Cu, Cu-62, Cu-64, Cu-67, Gd, Gd-153, Dy, Dy-165, Dy-166, Ho, Ho-166, Eu, Eu-169, Sm, Sm-153, Pd, Pd-103, Pm, Pm-149, Tm, Tm-170, Bi, Bi-212, As and As-211.

While not depicted in Formula (3), the hydroxyl or thiol groups of the ((di)thio)resorcinol derivative may independently participate in the coordination of the metal. Accordingly, in some embodiments, neither of the hydroxyl or thiol groups directly participate in the coordination of the metal, while in other embodiments one or both of the hydroxyl or thiol groups participate in the coordination of the metal. Both the nature of the metal selected and the particular metal coordinating moiety selected will determine whether the hydroxyl or thiol groups of the ((di)thio)resorcinol derivative participate in the coordination of the metal. Further, when the metal coordinating moiety comprises a resorcinol derivative, both of the oxygen atoms are involved in the bonding of the metal at one time or another due to the quilibrium present. Both hydroxyloxygens, however, are not bond to the same metal at the same time.

Alternatively, in one embodiment where the metal coordinating moiety comprises a chain of atoms and is complexed with a metal, M, the complex has the following Formula (4):

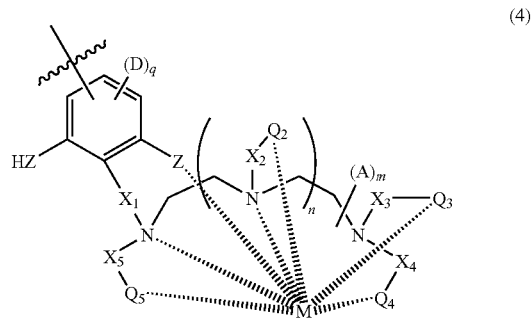

(4)

wherein
each Z is independently oxygen or sulfur;
n is 0, 1 or 2;
m is 0-12 wherein when m is greater than 0, each A is $C_{1-20}$alkyl or aryl optionally substituted by one or more aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto or thio;
q is 0-3 wherein when q is greater than 0, each D is independently selected from the group consisting of fluoro, chloro, bromo, Iodo, carboxyl, cyano, nitro, amido, hydroxyl, amino, sulfato, sulfito, phosphato, phosphito, ether, $C_{4-20}$ carbohydrate, aryl, and $C_{1-20}$ alkyl optionally substituted with one or more of $C_{1-20}$alkyl, carboxyl, cyano, nitro, amido, hydroxyl, amino, sulfato, sulfito, phosphato, and phosphito;
$X_1$, $X_2$, $X_3$, $X_4$ and $X_5$ are independently optionally substituted methylene where the substituents are selected from the group consisting of aryl, $C_{1-20}$alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto and thio;
$Q_2$-$Q_5$ are independently selected from the group consisting of:

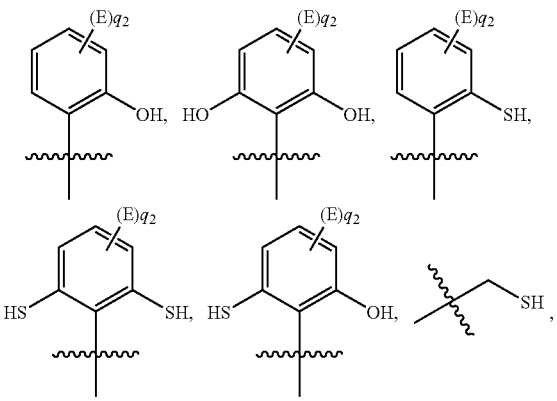

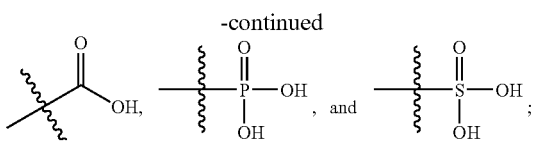

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, phosphito, phosphato, ether, $C_{4-20}$ carbohydrate, and $C_{1-20}$ alkyl optionally substituted with one or more of $C_{1-20}$ alkyl, carboxy, cyano, nitro, amido, hydroxyl, sulfito, phospito, sulfato, and phosphato; and M is selected from the group consisting of Lu, Lu-177, Y, Y-90, In, In-111, Tc, Tc=O, Tc-99m, Tc-99 m=O, Re, Re-186, Re-188, Re=O, Re-186=O, Re-188=O, Ga, Ga-67, Ga-68, Cu, Cu-62, Cu-64, Cu-67, Gd, Gd-153, Dy, Dy-165, Dy-166, Ho, Ho-166, Eu, Eu-169, Sm, Sm-153, Pd, Pd-103, Pm, Pm-149, Tm, Tm-170, Bi, Bi-212, As and As-211.

While not depicted in Formula (4), the hydroxyl and/or thiol groups of the ((di)thio)resorcinol derivative may independently participate in the coordination of the metal. Accordingly, in some embodiments, one of the hydroxyl or thiol groups, on a single ((di)thio)resorcinol derivative, directly participates in the coordination of the metal, while in other embodiments the other one of the hydroxyl or thiol groups participate in the coordination of the metal. In another embodiment, both groups participate at one time or another. For instance:

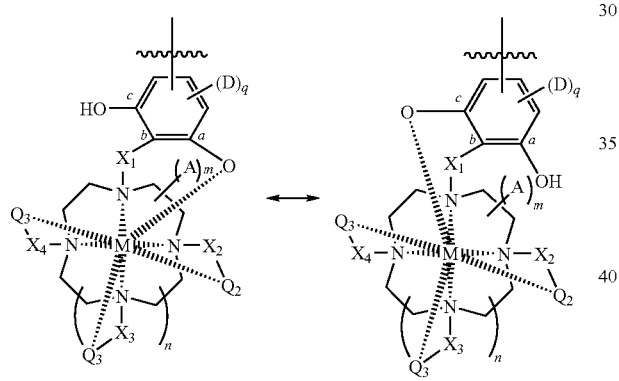

where the two oxygen atoms are interconverting due to breaking and reformation of M-O (letters a, b, and c are recited to better show the interconversion between the two oxygen atoms).

Both the nature of the metal selected and the particular metal coordinating moiety selected will determine whether the hydroxyl or thiol groups of the ((di)thio)resorcinol derivative participate in the coordination of the metal. Further, when the metal coordinating moiety comprises a resorcinol derivative, both of the oxygen atoms are involved in the bonding of the metal at one time or another due to the quilibrium present. Both hydroxyloxygens, however, are not bond to the same metal at the same time.

Whether the preferred complex corresponds to Formula (3) or Formula (4) typically depends on the particular metal selected for coordination. For example, for yttrium and lanthanides, the complex corresponding to Formula (3) is preferred. Formula (3) is also preferred for iron, copper, and manganese while Formula (4) is the preferred complex for the remaining transition metals. The preferred complex for any particular metal is related to the potential for transmetallation with endogenous ion. Thus, Formula (3) provides greater stability with high exchange metals, including, but not limited to, yttrium, lanthanides, and gallium. Transmetallation with endogenous ions does not present as great a concern for regular transition metals.

Macrocyclic metal coordinating moieties with three-dimensional cavities often form metal complexes with high stability. These complexes often exhibit selectivity for certain metal ions based on metal size and coordination chemistry, and capability to adopt a preorganized conformation in the uncomplexed form, which facilitates metal complexation. The selection of appropriate macrocyclic metal coordinating moieties and metals is known by those skilled in the art.

In addition, the preferred value of n, and hence the size or length of the metal coordinating moiety, depends upon the particular metal to be coordinated. For yttrium and lanthanides, for example, n is preferably 1. For transition metals, n is typically 0 or 1. For manganese and technetium, n is 0, 1, or 2 depending on the value of $X_1$-$X_4$.

General Synthesis

A general synthesis for the preparation of ((di)thio)resorcinol-bearing metal coordinating moieties is shown below.

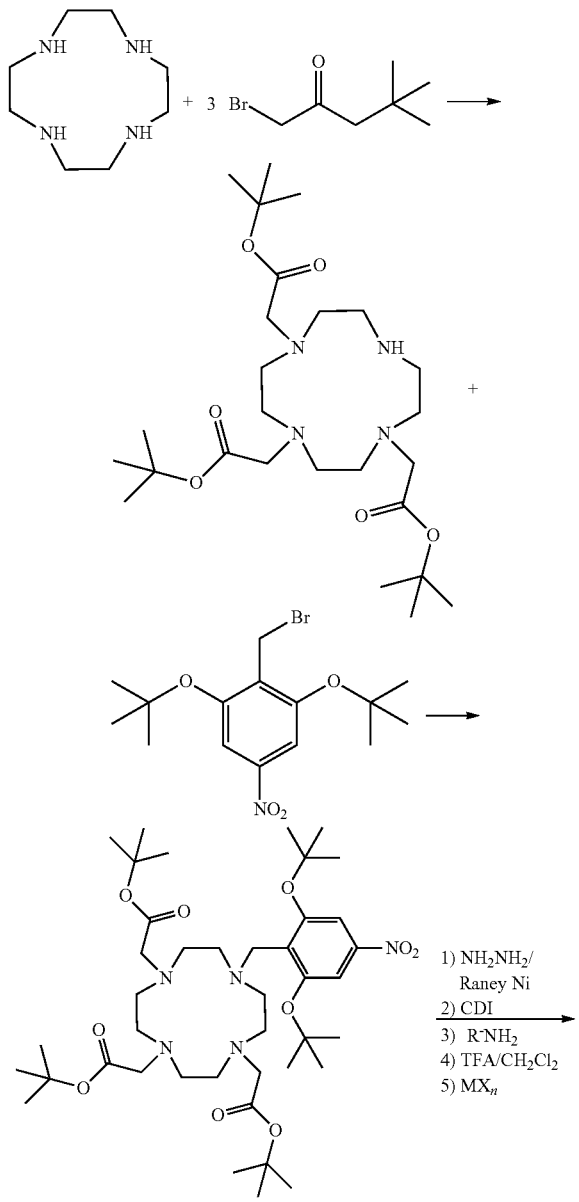

-continued

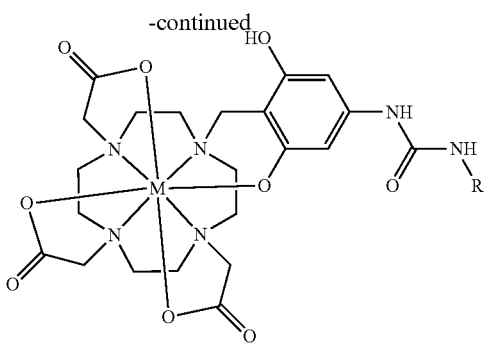

In this case, the amine portion of the metal chelator is cyclen, the ancillary coordinating moieties are carboxymethyl groups and the resorcinol-binding moiety is connected to the biodirecting carrier (designated as "R" in the scheme above) via a urea linkage.

Metallopharmaceutical Compositions

Metallopharmaceutical compositions of the present invention comprise a conjugate, complexed to a metal, dispersed in a pharmaceutically acceptable carrier. The pharmaceutically acceptable carrier, also known in the art as an excipient, vehicle, auxiliary, adjuvant, or diluent, is typically a substance which is pharmaceutically inert, confers a suitable consistency or form to the composition, and does not diminish the therapeutic or diagnostic efficacy of the conjugate. The carrier is generally considered to be "pharmaceutically or pharmacologically acceptable" if it does not produce an unacceptably adverse, allergic or other untoward reaction when administered to a mammal, especially a human.

The selection of a pharmaceutically acceptable carrier will also, in part, be a function of the route of administration. In general, the metallopharmaceutical compositions of the invention can be formulated for any route of administration so long as the target tissue is available via that route. For example, suitable routes of administration include, but are not limited to, oral, parenteral (e.g., intravenous, intraarterial, subcutaneous, rectal, subcutaneous, intramuscular, intraorbital, intracapsular, intraspinal, intraperitoneal, or intrasternal), topical (nasal, transdermal, intraocular), intravesical, intrathecal, enteral, pulmonary, intralymphatic, intracavital, vaginal, transurethral, intradermal, aural, intramammary, buccal, orthotopic, intratracheal, intralesional, percutaneous, endoscopical, transmucosal, sublingual and intestinal administration.

Pharmaceutically acceptable carriers for use in the compositions of the present invention are well known to those of ordinary skill in the art and are selected based upon a number of factors: the particular conjugate used, and its concentration, stability and intended bioavailability; the disease, disorder or condition being treated or diagnosed with the composition; the subject, its age, size and general condition; and the route of administration. Suitable nonaqueous, pharmaceutically-acceptable polar solvents include, but are not limited to, alcohols (e.g., α-glycerol formal, β-glycerol formal, 1,3-butyleneglycol, aliphatic or aromatic alcohols having 2-30 carbon atoms such as methanol, ethanol, propanol, isopropanol, butanol, t-butanol, hexanol, octanol, amylene hydrate, benzyl alcohol, glycerin (glycerol), glycol, hexylene glycol, tetrahydrofurfuryl alcohol, lauryl alcohol, cetyl alcohol, or stearyl alcohol, fatty acid esters of fatty alcohols such as polyalkylene glycols (e.g., polypropylene glycol, polyethylene glycol), sorbitan, sucrose and cholesterol); amides (e.g., dimethylacetamide (DMA), benzyl benzoate DMA, dimethylformamide, N-(β-hydroxyethyl)-lactamide, N,N-dimethylacetamide amides, 2-pyrrolidinone, 1-methyl-2-pyrrolidinone, or polyvinylpyrrolidone); esters (e.g., 1-methyl-2-pyrrolidinone, 2-pyrrolidinone, acetate esters such as monoacetin, diacetin, and triacetin, aliphatic or aromatic esters such as ethyl caprylate or octanoate, alkyl oleate, benzyl benzoate, benzyl acetate, dimethylsulfoxide (DMSO), esters of glycerin such as mono, di, or tri-glyceryl citrates or tartrates, ethyl benzoate, ethyl acetate, ethyl carbonate, ethyl lactate, ethyl oleate, fatty acid esters of sorbitan, fatty acid derived PEG esters, glyceryl monostearate, glyceride esters such as mono, di, or tri-glycerides, fatty acid esters such as isopropyl myristrate, fatty acid derived PEG esters such as PEG-hydroxyoleate and PEG-hydroxystearate, N-methylpyrrolidinone, pluronic 60, polyoxyethylene sorbitol oleic polyesters such as poly(ethoxylated)$_{30-60}$ sorbitol poly(oleate)$_{2-4}$, poly(oxyethylene)$_{15-20}$ monooleate, poly(oxyethylene)$_{15-20}$ mono 12-hydroxystearate, and poly(oxyethylene)$_{15-20}$ mono ricinoleate, polyoxyethylene sorbitan esters such as polyoxyethylene-sorbitan monooleate, polyoxyethylene-sorbitan monopalmitate, polyoxyethylene-sorbitan monolaurate, polyoxyethylene-sorbitan monostearate, and Polysorbate® 20, 40, 60 or 80 from ICI Americas, Wilmington, Del., polyvinylpyrrolidone, alkyleneoxy modified fatty acid esters such as polyoxyl 40 hydrogenated castor oil and polyoxyethylated castor oils (e.g., Cremophor® EL solution or Cremophor® RH 40 solution), saccharide fatty acid esters (i.e., the condensation product of a monosaccharide (e.g., pentoses such as ribose, ribulose, arabinose, xylose, lyxose and xylulose, hexoses such as glucose, fructose, galactose, mannose and sorbose, trioses, tetroses, heptoses, and octoses), disaccharide (e.g., sucrose, maltose, lactose and trehalose) or oligosaccharide or mixture thereof with a $C_4$-$C_{22}$ fatty acid(s) (e.g., saturated fatty acids such as caprylic acid, capric acid, lauric acid, myristic acid, palmitic acid and stearic acid, and unsaturated fatty acids such as palmitoleic acid, oleic acid, elaidic acid, erucic acid and linoleic acid)), or steroidal esters); alkyl, aryl, or cyclic ethers having 2-30 carbon atoms (e.g., diethyl ether, tetrahydrofuran, dimethyl isosorbide, diethylene glycol monoethyl ether); glycofurol (tetrahydrofurfuryl alcohol polyethylene glycol ether); ketones having 3-30 carbon atoms (e.g., acetone, methyl ethyl ketone, methyl isobutyl ketone); aliphatic, cycloaliphatic or aromatic hydrocarbons having 4-30 carbon atoms (e.g., benzene, cyclohexane, dichloromethane, dioxolanes, hexane, n-decane, n-dodecane, n-hexane, sulfolane, tetramethylenesulfon, tetramethylenesulfoxide, toluene, dimethylsulfoxide (DMSO), or tetramethylenesulfoxide); oils of mineral, vegetable, animal, essential or synthetic origin (e.g., mineral oils such as aliphatic or wax-based hydrocarbons, aromatic hydrocarbons, mixed aliphatic and aromatic based hydrocarbons, and refined paraffin oil, vegetable oils such as linseed, tung, safflower, soybean, castor, cottonseed, groundnut, rapeseed, coconut, palm, olive, corn, corn germ, sesame, persic and peanut oil and glycerides such as mono-, di- or triglycerides, animal oils such as fish, marine, sperm, cod-liver, haliver, squalene, squalane, and shark liver oil, oleic oils, and polyoxyethylated castor oil); alkyl or aryl halides having 1-30 carbon atoms and optionally more than one halogen substituent; methylene chloride; monoethanolamine; petroleum benzin; trolamine; omega-3 polyunsaturated fatty acids (e.g., alpha-linolenic acid, eicosapentaenoic acid, docosapentaenoic acid, or docosahexaenoic acid); polyglycol ester of 12-hydroxystearic acid and polyethylene glycol (Solutol® HS-15, from BASF, Ludwigshafen, Germany); polyoxyethylene glycerol; sodium laurate; sodium oleate; or sorbitan monooleate.

Other pharmaceutically acceptable solvents for use in the invention are well known to those of ordinary skill in the art, and are identified in *The Chemotherapy Source Book* (Williams & Wilkens Publishing), *The Handbook of Pharmaceutical Excipients*, (American Pharmaceutical Association, Washington, D.C., and The Pharmaceutical Society of Great Britain, London, England, 1968), *Modern Pharmaceutics*, (G. Banker et al., eds., 3d ed.)(Marcel Dekker, Inc., New York, N.Y., 1995), *The Pharmacological Basis of Therapeutics*, (Goodman & Gilman, McGraw Hill Publishing), *Pharmaceutical Dosage Forms*, (H. Lieberman et al., eds.)(Marcel Dekker, Inc., New York, N.Y., 1980), *Remington's Pharmaceutical Sciences* (A. Gennaro, ed., 19th ed.)(Mack Publishing, Easton, Pa., 1995), *The United States Pharmacopeia 24, The National Formulary 19*, (National Publishing, Philadelphia, Pa., 2000), A. J. Spiegel et al., and Use of Nonaqueous Solvents in Parenteral Products, JOURNAL OF PHARMACEUTICAL SCIENCES, Vol. 52, No. 10, pp. 917-927 (1963).

Dosage

Dosage and regimens for the administration of the pharmaceutical compositions of the invention can be readily determined by those with ordinary skill in diagnosing or treating disease. It is understood that the dosage of the conjugates will be dependent upon the age, sex, health, and weight of the recipient, kind of concurrent treatment, if any, frequency of treatment, and the nature of the effect desired. For any mode of administration, the actual amount of conjugate delivered, as well as the dosing schedule necessary to achieve the advantageous effects described herein, will also depend, in part, on such factors as the bioavailability of the conjugate, the disorder being treated or diagnosed, the desired therapeutic or diagnostic dose, and other factors that will be apparent to those of skill in the art. The dose administered to an animal, particularly a human, in the context of the present invention should be sufficient to affect the desired therapeutic or diagnostic response in the animal over a reasonable period of time.

Radiolabeled scintigraphic imaging agents provided by the present invention are provided having a suitable amount of radioactivity. In forming diagnostic radioactive complexes, it is generally preferred to form radioactive complexes in solutions containing radioactivity at concentrations of from about 0.01 millicurie (mCi) to 100 mCi per mL. Generally, the unit dose to be administered has a radioactivity of about 0.01 mCi to about 100 mCi, preferably about 1 mCi to about 30 mCi. The solution to be injected at unit dosage is from about 0.01 mL to about 10 mL. The amount of radiolabeled conjugate appropriate for administration is dependent upon the distribution profile of the chosen conjugate in the sense that a rapidly cleared conjugate may need to be administered in higher doses than one that clears less rapidly. In vivo distribution and localization can be tracked by standard scintigraphic techniques at an appropriate time subsequent to administration; typically between thirty minutes and 180 minutes depending upon the rate of accumulation at the target site with respect to the rate of clearance at the non-target tissue.

Typically, an In-111 diagnostic dose is 3-6 mCi while a typical Tc-99m does is 10-30 mCi. Generally, radiotherapeutic doses of radiopharmaceuticals vary to a greater extent, depending on the tumor and number of injections of cycles. For example, cumulative doses of Y-90 range from about 100-600 mCi (20-150 mCi/dose), while cumulative doses of Lu-177 range from about 200-800 mCi (50-200 mCi/dose).

Kits

For convenience, metallopharmaceutical compositions of the present invention may be provided to the user in the form of a kit containing some or all of the necessary components. The use of a kit is particularly convenient since some of the components, e.g., a radioisotope, have a limited shelf life, particularly when combined. Thus, the kit may include one or more of the following components (i) a conjugate, (ii) a metal coordinated to or for coordination by the conjugate, (iii) a carrier solution, and (iv) instructions for their combination and use. Depending on the metal, a reducing agent may be necessary to prepare the metal for reaction with the conjugate. Exemplary reducing agents include Ce(III), Fe(II), Cu(I), Ti(III), Sb(III), and Sn(II). Of these, Sn(II) is particularly preferred. Often the components of the kit are in unit dosage form (e.g., each component in a separate vial).

For reasons of stability, it may be preferred that the conjugate be provided in a dry, lyophilized state. The user may then reconstitute the conjugate by adding the carrier or other solution.

Because of the short half-life of suitable radionuclides, it will frequently be most convenient to provide the kit to the user without a radionuclide. The radionuclide is then ordered separately when needed for a procedure. Alternatively, if the radionuclide is included in the kit, the kit will most likely be shipped to the user just before it is needed.

In addition to the metal coordinating moiety, biomolecule, reactive electrophile (e.g., active urea, active ester, active alkylhalide, and acid chloride), metal and deprotecting acid, the kit of the present invention typically includes a buffer. Exemplary buffers include citrate, phosphate and borate.

The kit optionally contains other components frequently intended to improve the ease of synthesis of the radiopharmaceutical by the practicing end user, the ease of manufacturing the kit, the shelf-life of the kit, or the stability and shelf-life of the radiopharmaceutical. Such components of the present invention include lyophilization aids (e.g., mannitol, lactose, sorbitol, dextran, Ficoll, and polyvinylpyyrolidine (PVP)); stabilization aids (e.g., ascorbic acid, cysteine, monothioglycerol, sodium bisulfite, sodium metabisulfite, gentisic acid, and inositol); and bacteriostats (e.g., benzyl alcohol, benzalkonium chloride, chlorbutanol, and methyl, propyl, and butyl paraben).

Typically, when the conjugate is formulated as a kit, the kit comprises multiple vials consisting of a protected metal coordinating moiety having an active urea group, a deprotecting acid, a buffer, and a solution of a radioactive metal such as, but not limited to, In-111, Y-90 or Lu-177. In practice, the user will take the vial containing the metal coordinating moiety and add a solution of a bio-directing carrier of interest bearing a reactive amino ($NH_2$) group. Once conjugation is complete, the deprotecting acid is added to affect deprotection, followed by addition of the radioactive metal. The mixture is then buffered to complete complexation of the radioactive metal by the metal chelator.

DEFINITIONS

The compounds described herein may have asymmetric centers. Compounds of the present invention containing an asymmetrically substituted atom may be isolated in optically active or racemic form. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The present invention includes all isotopes of atoms occurring in the present compounds. Isotopes include those atoms having the same atomic number but different mass numbers.

Unless otherwise indicated, the alkyl groups described herein are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "amido" as used herein includes substituted amido moieties where the substituents include, but are not limited to, one or more of aryl and $C_{1-20}$ alkyl, each of which may be optionally substituted by one or more aryl, carbaldehyde, keto, carboxyl, cyano, halo, nitro, $C_{1-20}$ alkyl, sulfato, sulfito, phosphato, phosphito, hydroxyl, oxy, mercapto, and thio substituents.

The term "amino" as used herein includes substituted amino moieties where the substituents include, but are not limited to, one or more of aryl and $C_{1-20}$ alkyl, each of which may be optionally substituted by one or more aryl, carbaldehyde, keto, carboxyl, cyano, halo, nitro, $C_{1-20}$ alkyl, sulfato, sulfito, phosphato, phosphito, hydroxyl, oxy, mercapto, and thio substituents.

The terms "aryl" or "ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "complex" refers to a metal coordinating moiety of the invention, e.g. Formula (1), complexed or coordinated with a metal. The metal is typically a radioactive isotope or paramagnetic metal ion.

The term "conjugate" refers to a metal coordinating moiety of the invention, e.g. Formula (1), bonded to a bio-directing carrier (biomolecule) whether or not the metal coordinating moiety is complexed with a metal. For the present invention, the metal coordinating moiety is bonded to the bio-directing carrier directly or indirectly by a urea moiety.

The terms "halogen" or "halo" as used herein alone or as part of another group refer to chlorine, bromine, fluorine, and iodine.

The term "heteroatom" shall mean atoms other than carbon and hydrogen.

The terms "heterocyclo" or "heterocyclic" as used herein alone or as part of another group denote optionally substituted, fully saturated or unsaturated, monocyclic or bicyclic, aromatic or nonaromatic groups having at least one heteroatom in at least one ring. The heterocyclo group preferably has 1 to 5 nitrogen atoms in the ring, and may be bonded to the remainder of the molecule through a carbon atom. Exemplary heterocyclics include macrocyclics, cyclen, DOTA, DOTMA, DOTP, and TETA.

The "heterosubstituted alkyl" moieties described herein are alkyl groups in which a carbon atom is covalently bonded to at least one heteroatom and optionally with hydrogen, the heteroatom being, for example, a nitrogen atom.

The term "metallopharmaceutical" as used herein refers to a pharmaceutically acceptable compound comprising a metal, wherein the compound is useful for imaging or treatment.

As used herein, a "resorcinol derivative" comprises a m-dihydroxybenzne moiety.

As used herein, a "thioresorcinol derivative" comprises a resorcinol derivative wherein one of the hydroxyl groups has been replaced by a thiol moiety.

As used herein, a "dithioresorcinol derivative" comprises a resorcinol derivative wherein both of the hydroxyl groups have been replaced by thiol groups.

EXAMPLES

The following examples are prophetic.

Example 1

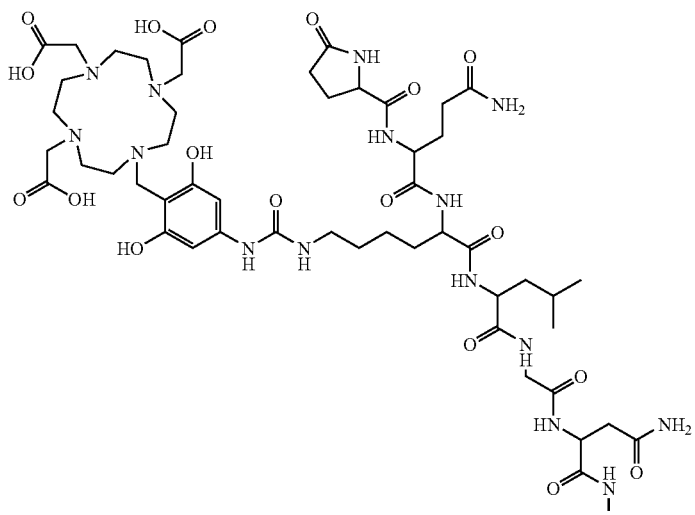

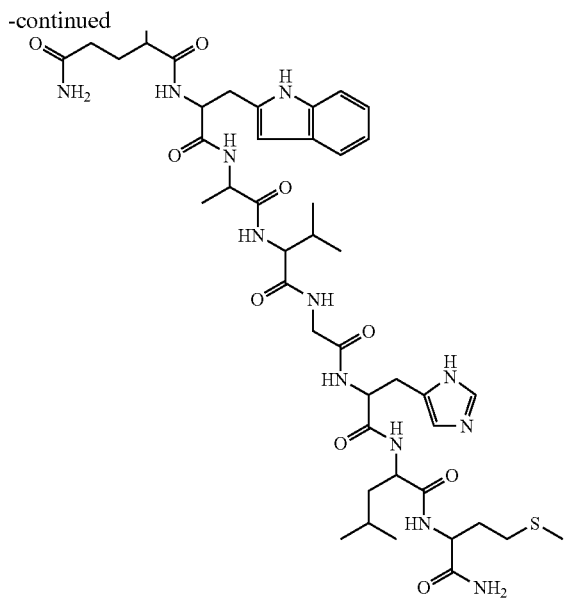

1,4,7,10-Tetraazacyclododecane-1,4,7-triacetic acid, tris (1,1-dimethylethyl) ester is allowed to react with 2-(bromomethyl)-1,3-di-tert-butoxy-5-nitrobenzene in acetonitrile with sodium bicarbonate as the base. The resulting product is isolated by crystallization from the reaction mixture and treated with hydrazine and raney nickel to reduce the nitro group. The resulting aniline is treated with CDI and that intermediate allowed to react with bombesin$_{1-14}$(lys$^3$). The product is purified by reverse phase chromatography, dissolved in a 1:1 mixture of trifluoroacetic acid:dichloromethane and evaporated to give the deprotected ligand-conjugate. This is allowed to react with indium-111 to give the prophetic diagnostic agent for GRP-positive cancer detection.

Example 2

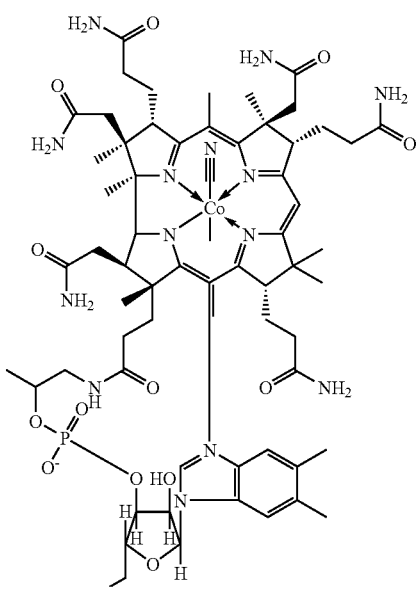

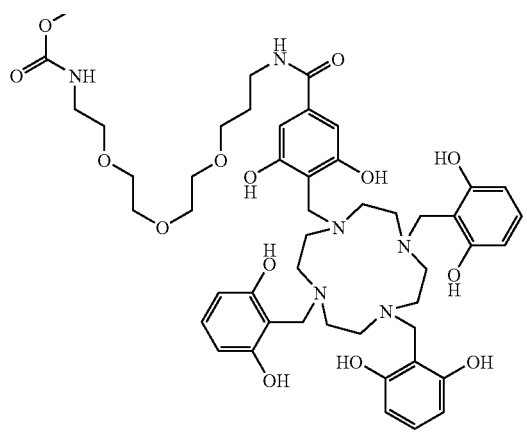

Cyclen is selectively trialkylated with 2-(bromomethyl)-1,3-di-t-butoxybenzene to give 1,4,7,10-Tetraazacyclododecane-1,4,7-tris(2-yl(1,3-di-t-butoxybenzenemethyl). This amine is alkylated with t-butyl 4-(bromomethyl)-3,5-di-t-butoxybenzoate. The t-butyl ester is removed by treatment with formic acid and the resulting carboxylic acid conjugated to the amino ether of 5'-carbamoyl-modified CNCbl as per Horton et al, JOC, 68 (18), 7108-7111, 2003. The t-butyl ether groups are removed by treatment with trifluoromethansulfonic acid in trifluoroethanol.

What is claimed is:
1. A conjugate comprising a bio-directing carrier, a metal coordinating moiety, and a linker chemically linking the metal coordinating moiety to the carrier, the metal coordinating moiety comprising a resorcinol, thioresorcinol, or dithioresorcinol derivative, wherein:

(i) the metal coordinating moiety comprises a substituted heterocyclic ring having the following structure:

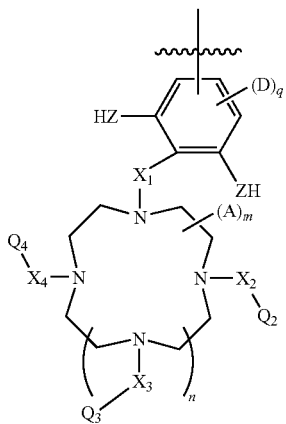

(1)

wherein each Z is independently oxygen or sulfur;

n is 0, 1 or 2;

m is 0-20 wherein when m is greater than 0, each A is $C_{1-20}$ alkyl or aryl optionally substituted by one or more aryl, $C_{1-20}$ alkyl, carbaldehyde keto, carboxyl, cyano, halo, nitro, amido, sulfato, sulfito, phosphato, phosphito, hydroxyl, oxy, ether, $C_{4-20}$ carbohydrate, mercapto or thiol;

q is 0-3 wherein when q is greater than 0, each D is independently selected from the group consisting of fluoro, chloro, bromo, iodo, carboxyl, cyano, nitro, amido, hydroxyl, amino, sulfato, sulfito, phosphato, phosphito, ether $C_{4-20}$ carbohydrate, aryl, and $C_{1-20}$ alkyl optionally substituted with one or more of $C_{1-20}$ alkyl, carboxyl, cyano, nitro, amido, hydroxyl, amino, sulfato, sulfito, phosphato, and phosphito;

$X_1, X_2, X_3$ and $X_4$ are independently optionally substituted methylene where the substituents are selected from the group consisting of aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto and thio;

$Q_2$-$Q_4$ are independently selected from the group consisting of:

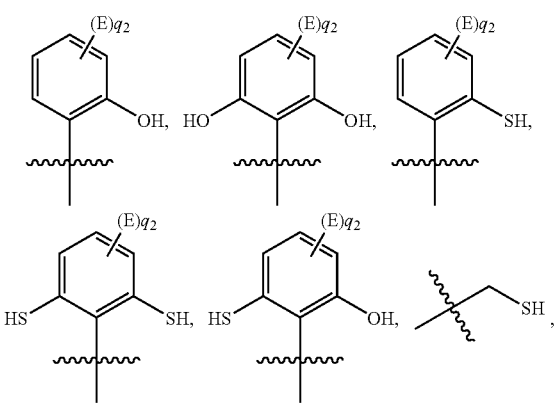

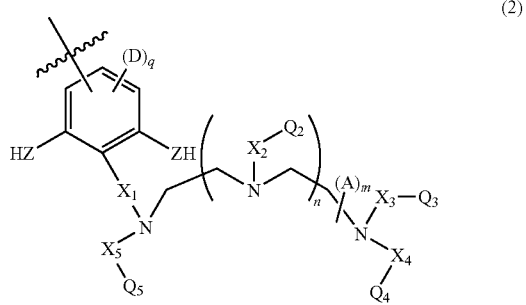

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, phosphito, phosphato, ether, $C_{4-20}$ carbohydrate, and $C_{1-20}$ alkyl optionally substituted with one or more of $C_{1-20}$ alkyl, carboxy, cyano, nitro, amido, hydroxyl, sulfito, phospito, sulfato, and phosphate; or (ii) the metal coordinating moiety comprises a substituted chain of carbon and nitrogen atoms having the following structure:

(2)

wherein each Z is independently oxygen or sulfur;

n is 0, 1 or 2;

m is 0-12 wherein when m is greater than 0, each A is $C_{1-20}$ alkyl or aryl optionally substituted by one or more aryl, $C_{1-20}$ alkyl, carbaldehyde, keto, carboxyl, cyano, halo, nitro, amido, sulfato, sulfito, phosphato, phosphito, hydroxyl, oxo, ether, $C_{4-20}$ carbohydrate, mercapto or thio;

q is 0-3 wherein when q is greater than 0, each D is independently selected from the group consisting of fluoro, chloro, bromo, iodo, carboxyl, cyano, nitro, amido, hydroxyl, amino, sulfato, sulfito, phosphato, phosphito, ether, $C_{4-20}$ carbohydrate, aryl, and $C_{1-20}$ alkyl optionally substituted with one or more of $C_{1-20}$ alkyl, carboxyl, cyano, nitro, amido, hydroxyl, amino, sulfato, sulfito, phosphato, and phosphito;

$X_1, X_2, X_3, X_4$, and $X_5$ are independently optionally substituted methylene where the substituents are selected from the group consisting of aryl, $C_{1-20}$ alkyl, carbaldehyde keto, carboxyl, cyano, halo, nitro, amido, sulfato, sulfito, phosphato, phosphito, hydroxyl, oxo, ether, $C_{4-20}$ carbohydrate, mercapto and thio;

$Q_2$-$Q_5$ are independently from the group consisting of:

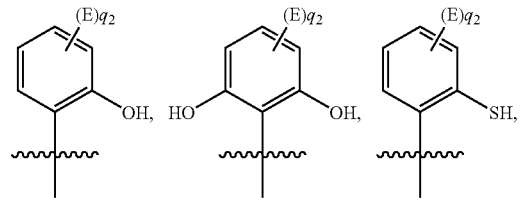

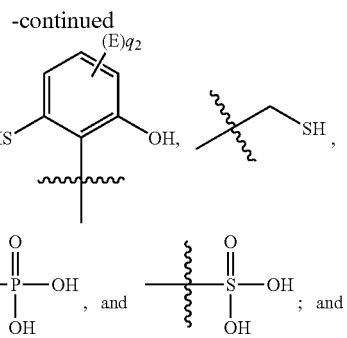

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, phosphito, phosphato, ether, $C_{4-20}$ carbohydrate, and $C_{1-20}$ alkyl optionally substituted with one or more of $C_{1-20}$ alkyl, carboxy cyano, nitro, amido, hydroxyl, sulfito, phospito, sulfato, and phosphate.

2. The conjugate of claim 1 wherein the bio-directing carrier is selected from the group consisting of imidazole, triazole, antibodies, proteins, peptides, carbohydrates, vitamins, hormones, drugs, and small organic molecules.

3. The conjugate of claim 1 wherein the conjugate comprises more than one bio-directing carrier.

4. The conjugate of claim 1 wherein the metal coordinating moiety is complexed with a metal, the metal consisting of a radioisotope or a paramagnetic metal.

5. The conjugate of claim 4 wherein the metal is selected from the group consisting of Lu, Lu-177, Y, Y-90, In, In-111, Tc, Tc=O, Tc-99m, Tc-99m=O, Re, Re-186, Re-188, Re=O, Re-186=O, Re-188=0, Ga, Ga-67, Ga-68, Cu, Cu-62, Cu-64, Cu-67, Gd, Gd-153, Dy, Dy-165, Dy-166, Ho, Ho-166, Eu, Eu-169, Sm, Sm-153, Pd, Pd-103, Pm, Pm-149, Tm, Tm-170, Bi, Bi-212, As and As-211.

6. The conjugate of claim 1 wherein the linker is selected from the group consisting of $C_{1-10}$ alkylene, oxygen, sulfur, keto, amino, amido, urea, thiourea, and ester, the alkylene, amino, amido, urea, and thiourea groups being optionally substituted with aryl, $C_{1-7}$ alkyl, $C_{1-7}$ hydroxyalkyl or $C_{1-7}$ alkoxyalkyl.

7. The conjugate of claim 6 wherein the linker is selected from the group consisting of C1-10 alkylene, oxygen, sulfur, keto, amino, amido, thiourea, and ester.

8. The conjugate of claim 1 wherein the metal coordinating moiety is complexed with a metal, M, forming a metal complex having the formula

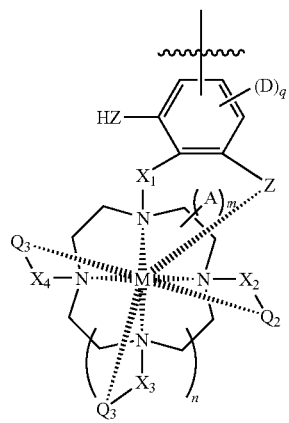

(3)

wherein
each Z is independently oxygen or sulfur;
n is 0, 1 or 2;
m is 0-20 wherein when m is greater than 0, each A is $C_{1-20}$ alkyl or aryl optionally substituted by one or more aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto or thio;

q is 0-3 wherein when q is greater than 0, each D is independently selected from the group consisting of fluoro, chloro, bromo, Iode, carboxyl, cyano, nitro, amido, hydroxyl, amino, sulfato, sulfito, phosphato, phosphito, ether, $C_{4-20}$ carbohydrate, aryl, and $C_{1-20}$ alkyl optionally substituted with one or more of $C_{1-20}$ alkyl, carboxyl, cyano, nitro, amido, hydroxyl, amino, sulfato, sulfito, phosphato, and phosphito;

$X_1$, $X_2$, $X_3$ and $X_4$ are independently optionally substituted methylene where the substituents are selected from the group consisting of aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto and thio;

$Q_2$-$Q_4$ are independently selected from the group consisting of:

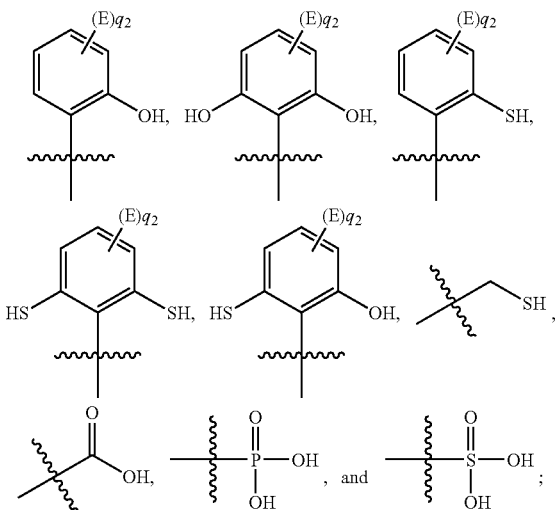

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, phosphito, phosphato, ether, $C_{4-20}$ carbohydrate, and $C_{1-20}$ alkyl optionally substituted with one or more of $C_{1-20}$ alkyl, carboxy, cyano, nitro, amido, hydroxyl, sulfito, phospito, sulfato, and phosphate; and M is selected from the group consisting of Lu, Lu-177, Y, Y-90, In, In-111, Tc, Tc=O, Tc-99m, Tc-99m=O, Re, Re-186, Re-188, Re=O, Re-186=O, Re-188=O, Ga, Ga-67, Ga-68, Cu, Cu-62, Cu-64, Cu-67, Gd, Gd-153, Oy, Dy-165, Dy-166, Ho, Ho-166, Eu, Eu-169, Sm, Sm-153, Pd, Pd-103, Pm, Pm-149, Tm, Tm-170, Bi, Bi-212, As and As-211.

9. The conjugate of claim 1 wherein the metal coordinating moiety is complexed with a metal, M, forming a metal complex having the formula (4)

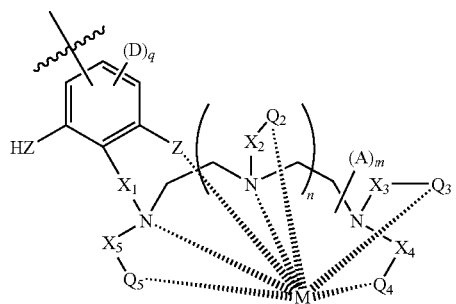

wherein
each Z is independently oxygen or sulfur;
n is 0, 1 or 2;
m is 0-12 wherein when m is greater than 0, each A is $C_{1-20}$ alkyl or aryl optionally substituted by one or more aryl, $C_{1-20}$ alkyl, carbaldehyde, keto, carboxyl, cyano, halo; nitro, amido, sulfato, sulfito, phosphato, phosphito, hydroxyl, oxy, ether, $C_{4-20}$ carbohydrate, mercapto or thio;
q is 0-3 wherein when q is greater than 0, each D is independently selected from the group consisting of fluoro, chloro, bromo, Iode, carboxyl, cyano, nitro, amido, hydroxyl, amino, sulfato, sulfito, phosphato, phosphito, ether, $C_{4-20}$ carbohydrate, aryl, and $C_{1-20}$ alkyl optionally substituted with one or more of $C_{1-20}$ alkyl, carboxyl, cyano, nitro, amido, hydroxyl, amino, sulfato, sulfito, phosphato, and phosphito;
$X_1$, $X_2$, $X_3$, $X_4$ and $X_5$ are independently optionally substituted methylene where the substituents are selected from the group consisting of aryl, $C_{1-20}$ alkyl, carbaldehyde, keto, carboxyl, cyano, halo, nitro, amido, sulfato, sulfito, phosphato, phosphito, hydroxyl, oxy, ether, $C_{4-20}$ carbohydrate, mercapto and thio;
$Q_2$-$Q_5$ are independently selected from the group consisting of:

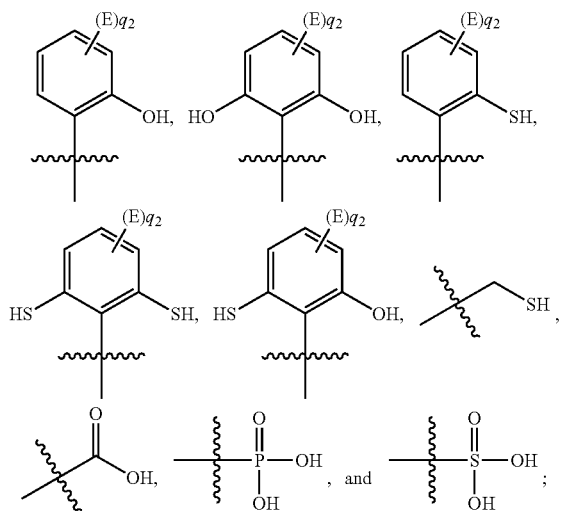

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, phosphito, phosphato, ether, $C_{4-20}$ carbohydrate, and $C_{1-20}$ alkyl optionally substituted with one or more of $C_{1-20}$ alkyl, carboxy, cyano, nitro, amido, hydroxyl, sulfito, phospito, sulfato, and phosphato; and M is selected from the group consisting of Lu, Lu-177, Y, Y-90, In, In-111, Tc, Tc=O, Tc-99m, Tc-99m=O, Re, Re-186, Re-188, Re=O, Re-186=O, Re-188=O, Ga, Ga-67, Ga-68, Cu, Cu-62, Cu-64, Cu-67, Gd, Gd-153, Oy, Oy-165, Oy-166, Ho, Ho-166, Eu, Eu-169, Sm, Sm-153, Pd, Pd-103, Pm, Pm-149, Tm, Tm-170, Bi, Bi-212, As and As-211.

10. The conjugate of claim 1 wherein the metal coordinating complex comprises a resorcinol derivative.

11. A pharmaceutical composition comprising the conjugate of claim 1 and a pharmaceutically acceptable carrier.

12. A method for diagnosing cancer, the method comprising administering the pharmaceutical composition of claim 11 to a subject.

13. A method for treating of cancer, the method comprising administering the pharmaceutical composition of claim 11 to a subject afflicted with cancer.

14. A kit comprising a metal coordinating moiety having a resorcinol, thioresorcinol, or dithioresorcinol derivative, a reactive electrophile, a deprotecting acid, and a buffer wherein the metal coordinating moiety comprises one of the following structures:

(1)

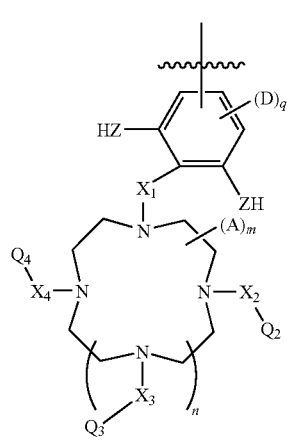

wherein
each Z is independently oxygen or sulfur;
n is 0, 1 or 2;
m is 0-20 wherein when m is greater than 0, each A is $C_{1-20}$ alkyl or aryl optionally substituted by one or more aryl, $C_{1-20}$ alkyl, carbaldehyde, keto, carboxyl, cyano, halo, nitro, amido, sulfato, sulfito, phosphato, phosphito, hydroxyl, oxy, mercapto or thio;
q is 0-3 wherein when q is greater than 0, each D is independently selected from the group consisting of fluoro, chloro, bromo, iodo, carboxyl, cyano, nitro, amido, hydroxyl, amino, sulfato, sulfito, phosphato, phosphito, aryl, and $C_{1-20}$ alkyl optionally substituted with one or more of $C_{1-20}$ alkyl, carboxyl, cyano, nitro, amido, hydroxyl, amino, sulfato, sulfito, phosphato, and phosphito;
$X_1$, $X_2$, $X_3$ and $X_4$ are independently optionally substituted methylene where the substituents are selected from the group consisting of aryl, $C_{1-20}$ alkyl, carbaldehyde, keto, carboxyl, cyano, halo, nitro, amido, sulfato, sulfito, phosphato, phosphito, hydroxyl, oxy, mercapto and thio;

$Q_2$-$Q_4$ are independently selected from the group consisting of:

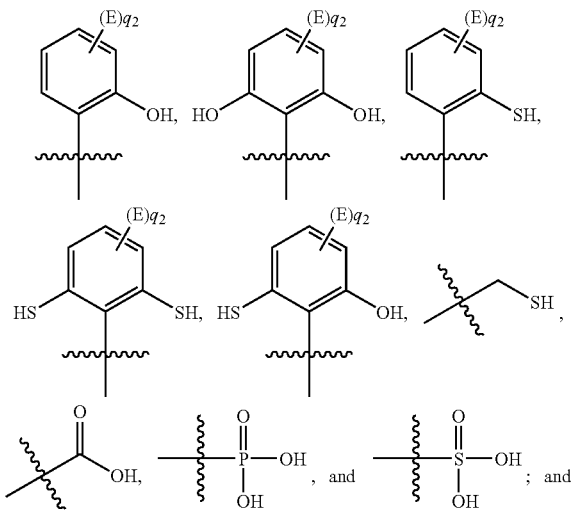

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, phosphito, phosphato, and $C_{1-20}$ alkyl optionally substituted with one or more of $C_{1-20}$ alkyl, carboxy, cyano, nitro, amido, hydroxyl, sulfito, phospito, sulfato, and phosphato; or

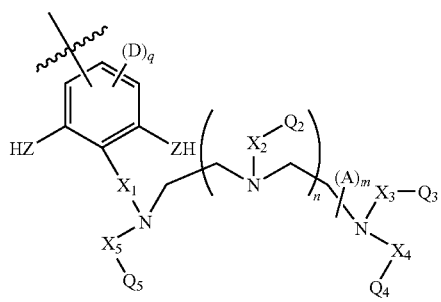
(2)

wherein
each Z is independently oxygen or sulfur;
n is 0, 1 or 2;
m is 0-12 wherein when m is greater than 0, each A is $C_{1-20}$ alkyl or aryl optionally substituted by one or more aryl, $C_{1-20}$ alkyl, carbaldehyde, keto, carboxyl, cyano, halo, nitro, amido, sulfato, sulfito, phosphato, phosphito, hydroxyl, oxy, mercapto or thio;
q is 0-3 wherein when q is greater than 0, each D is independently selected from the group consisting of fluoro, chloro, bromo, iodo, carboxyl, cyano, nitro, amido, hydroxyl, amino, sulfato, sulfito phosphato, phosphito, aryl, and $C_{1-20}$ alkyl optionally substituted with one or more of $C_{1-20}$ alkyl, carboxyl, cyano, nitro, amido, hydroxyl, amino, sulfato, sulfito, phosphato, and phosphito;
$X_1$, $X_2$, $X_3$, $X_4$, and $X_5$ are independently optionally substituted methylene where the substituents are selected from the group consisting of aryl, $C_{1-20}$ alkyl, carbaldehyde, keto, carboxyl, cyano, halo, nitro, amido, sulfato, sulfito, phosphato, phosphito, hydroxyl, oxy, mercapto and thio;
$Q_2$-$Q_5$ are independently selected from the group consisting of:

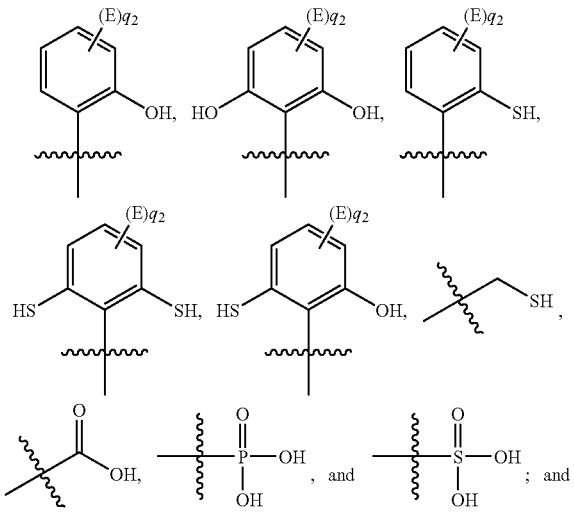

$q_2$ is 0-4 wherein when $q_2$ is greater than 0, each E is independently selected from the group consisting of fluoro, chloro, bromo, iodo, carboxyl, cyano, nitro, amido, hydroxyl, amino, sulfito, phosphito, phosphato, and $C_{1-20}$ alkyl optionally substituted with one or more of $C_{1-20}$ alkyl, carboxy, cyano, nitro, amido, hydroxyl, sulfito, phospito, sulfato, and phosphato.

15. The kit of claim 14 wherein the buffer is selected from the group consisting of citrate, phosphate and borate.

16. The kit of claim 14 wherein the reactive electrophile is selected from the group consisting of active urea, active ester, and active alkylhalide.

17. The kit of claim 14 wherein the metal coordinating moiety, the reactive electrophile, the deprotecting acid, and the buffer are in unit dosage form.

18. The kit of claim 14 wherein the kit additionally comprises a solution of a radioactive metal.

19. The kit of claim 18 wherein the radioactive metal is selected from the group consisting of Lu, Lu-177, Y, Y-90, In, In-111, Tc, Tc=O, Tc-99m, Tc-99m=O, Re, Re-186, Re-188, Re=O, Re-186=O, Re-188=O, Ga, Ga-67, Ga-68, Cu, Cu-62, Cu-64, Cu-67, Gd, Gd-153, Dy, Dy-165, Dy-166, Ho, Ho-166, Eu, Eu-169, Sm, Sm-153, Pd, Pd-103, Pm, Pm-149, Tm, Tm-170, Bi, Bi-212, As and As-211.

20. The kit of claim 19 wherein the metal coordinating moiety comprises a resorcinol derivative.

* * * * *